United States Patent [19]

Connor et al.

[11] Patent Number: 5,302,597

[45] Date of Patent: Apr. 12, 1994

[54] 2-SUBSTITUTED-4,6-DI-TERTIARYBUTYL-5-HYDROXY-1,3-PYRIMIDINES USEFUL AS ANTIINFLAMMATORY AGENTS

[75] Inventors: David T. Connor, Ann Arbor; Catherine R. Kostlan, Saline, both of Mich.

[73] Assignee: Warner-Lambert Company, Morris Plains, N.J.

[21] Appl. No.: 875,151

[22] Filed: Jun. 10, 1993

Related U.S. Application Data

[62] Division of Ser. No. 924,713, Aug. 3, 1992, Pat. No. 5,248,682, which is a division of Ser. No. 648,115, Jan. 31, 1991, Pat. No. 5,177,079.

[51] Int. Cl.$^5$ .................. A61K 31/505; C07D 239/02
[52] U.S. Cl. ..................................... 514/269; 544/298
[58] Field of Search ................. 544/298; 514/269; A61K 31/505

[56] References Cited

U.S. PATENT DOCUMENTS

| | | | |
|---|---|---|---|
| 4,554,276 | 11/1985 | LaMattina | 544/298 |
| 4,711,888 | 12/1987 | Walker et al. | 514/269 |
| 4,859,679 | 8/1989 | Santini | 514/273 |
| 4,940,712 | 7/1990 | Walker et al. | 514/272 |

FOREIGN PATENT DOCUMENTS

| | | |
|---|---|---|
| 0164204 | 12/1985 | European Pat. Off. |
| 0210044 | 1/1987 | European Pat. Off. |
| 0373827 | 6/1990 | European Pat. Off. |
| 1476534 | 5/1965 | France |

OTHER PUBLICATIONS

Derwent Abst. 46267c/27 (May 30, 1800).
Derwent Abst 89-29576/41 (Aug. 30, 1989).
Derwent Abst. 89 167195/23 (Jun. 7, 1989).
Derwent Abst 87 236597/34 (Aug. 26, 1987).
Derwent Abst 85-312102/50 (Dec. 1985).
J. Med. Chem., 1990, 33, pp. 1892-1898; Lazer, et al.
J.C.S. Perkin I, 1976, pp. 1202-1204; Roeterdink, et al.
Chem. Ber., 1960, pp. 1998-2001; Dornow, et al.
Indian Journal of Chemistry, vol. 24B, 1985, pp. 535-538; Sen, et al.
Chemical Reviews, 1975, vol. 75, No. 4, pp. 207 and 412.
Biochem, 1951, vol. 48, pp. 400-407; Bray, et al.

Primary Examiner—Cecilia Tsang
Attorney, Agent, or Firm—Ronald A. Daignault; Elizabeth M. Anderson

[57] ABSTRACT

The present invention is novel compounds which are 2-substituted-4,6-di-tertiarybutyl-5-hydroxy-1,3-pyrimidines and pharmaceutically acceptable acid addition or base salts thereof, pharmaceutical compositions and methods of use therefor. The invention compounds are now found to have activity as inhibitors of 5-lipoxygenase and/or cyclooxygenase providing treatment of conditions advantageously affected by such inhibition including inflammation, arthritis, pain, fever and the like. Thus, the present invention is also a pharmaceutical composition or method of manufacturing a pharmaceutical composition for the use of treating the noted conditions.

9 Claims, No Drawings

2-SUBSTITUTED-4,6-DI-TERTIARYBUTYL-5-HYDROXY-1,3-PYRIMIDINES USEFUL AS ANTIINFLAMMATORY AGENTS

This is a divisional of U.S. application Ser. No. 07/924,713 filed Aug. 3, 1992, now U.S. Pat. No. 5,248,682, which is a divisional of U.S. application Ser. No. 07/648,115 filed Jan. 31, 1991, now U.S. Pat. No. 5,177,079 granted Jan. 5, 1993.

BACKGROUND OF THE INVENTION

The present invention is novel compounds which are 2-substituted-4,6-di-tertiary-butyl-5-hydroxy-1,3-pyrimidines and pharmaceutically acceptable acid addition or base salts thereof, pharmaceutical compositions and methods of use therefor. The invention compounds are now found to have activity as inhibitors of 5-lipoxygenase and/or cyclooxygenase providing treatment of conditions advantageously affected by such inhibition including, for example, rheumatoid arthritis, osteoarthritis, other inflammatory conditions, pain, fever, psoriasis, allergic diseases, asthma, inflammatory bowel disease, GI ulcers, cardiovascular conditions including ischemic heart disease and atherosclerosis, and ischemia-induced cell damage, particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. However, overall the preferable use is to treat inflammatory conditions. Thus, the present invention is also a pharmaceutical composition or method of manufacturing a pharmaceutical composition for the use of treating the noted conditions.

3,5-Di-tertiary-butyl-4-hydroxybenzene, substituted by 1,2,4- and 1,3,4-thiadiazoles and oxadiazoles, and 1,2,4-triazoles are known to provide activity as inhibitors of 5-lipoxygenase and/or cyclooxygenase. See 3815-P1. Pyrimidine is not noted in this reference. Structure activity relationships of certain ditertiarybutyl phenols and homologs thereof are discussed by Lazer, E. S., et al in "Effect of Structure on Potency and Selectivity in 2,6-Disubstituted 4-(2-Arylethenyl)-phenol Lipoxygenase Inhibitors, *J. Med. Chem.* 1990, 33, 1982–1998. Again pyrimidines are not noted in this reference and so compounds therein differ from the present invention.

Numerous references disclose 2-amino-5-hydroxy pyrimidines. Compounds having N containing groups in place of the amino are also disclosed, however, in each such compounds attachment is through the N. Such disclosed pyrimidines may also be substituted at the 4- and/or 6-positions with various groups including alkyls. No reference shows a tertiarybutyl in both the 4- and 6-positions in combination with a 5-hydroxy together with a group other than the N or S containing substituent in the 2-position as found in the present invention. For example, UK patent application number 2045736 and the *Bioch. J.* 1951, 48, p. 400 shows the simple 2-amino-5-hydroxy-4,6-dimethylpyrimidine. Other substituted 2-aminopyridines are shown in European Patent Application Numbers 89312736.5 and 86305466.4 (equivalent to U.S. Pat. No. 4711888), European Publication Numbers 319170, 233416, 1642 and U.S. Pat. Nos. 4,859,679 and 4,940,712.

Japanese Application No. 1,216,978 discloses 2-arylpyrimidines but differs from the present invention, that requires the 4,6-di-tertiary-butyl-5-hydroxy substituents.

The difficulty of accommodating steric hindrance in the synthesis of 4,6-tertiarybutyl pyrimidine is documented in J. C. S. Perkin I (1976) 1202–4. No '5-OH' is considered in this synthesis. Further, although French application No. 1,476,534 presents a generic scope including various 2-substituted pyrimidines, this French application differs from the present invention by failing to provide the present invention substituent combinations.

The disclosures in *Chem. Ber.* (1960) pp. 1998–2001 and in the *Indian Journal of Chemistry*, Vol. 24B, May 1985, pp. 535–538 showing oxazole to pyrimidine ring transformations and the disclosure in *Chemical Reviews* (1975), Vol. 75, No. 4, pp. 207 and 412 showing a preparation of an oxazole and subsequent transformation to pyrimidine all show a synthesis and product having substituents in the 4- and 6-positions offering little or no steric hindrance contrary to the present invention which contains 4,6-ditertiarybutyl together with a 5-hydroxy substituent.

In summary, the references of record show neither the present 2-substituent nor combinations of 4 and 6 substituents with a 5-hydroxy group and particularly combinations in which the 4 and 6 substituents are ditertiarybutyl groups which provide steric hindrance not previously present during synthesis of pyrimidines.

SUMMARY OF THE INVENTION

The present invention is a compound of the formula I

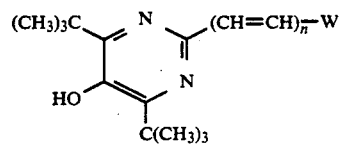

or pharmaceutically acceptable salt and hydrates thereof; wherein n is zero or one; and W is phenyl, substituted phenyl, naphthyl, substituted naphthyl or a 5- or 6-membered heteroaromatic ring 1) which ring contains 1, 2 or 3 heteroatoms selected from S, O, or N wherein the heteroaromatic ring may not have more than one of O or S, 2) which ring is attached at a carbon in the ring, and 3) which rings are optionally substituted by lower alkyl, preferably methyl. Of course the lower alkyl will be understood to be attached at one or more of the ring carbons.

The present invention is also a compound of the formula 4

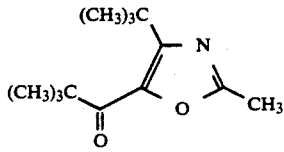

The present invention is also a compound of the formula 5

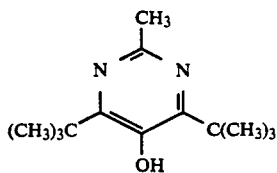

The present invention is also a compound of the formula 10

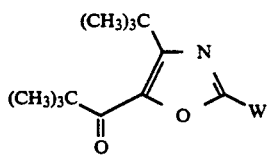

wherein W is as defined above.

Each of compounds 4, 5 and 10 are intermediates useful in the preparation of the compounds I defined herein.

The present invention is a method for the preparation of a compound of the formula 5 which comprises treating a compound of the formula 4 with concentrated ammonium hydroxide or with another agent which provides ammonia in situ but preferably with ammonium hydroxide by heating from room temperature to a temperature of 150° to 200° C., preferably at 180° C. in a pressure reactor.

The present invention is also a method of using the compound of the formula 4 to prepare the compound of formula 5 which comprises treating the compound of formula 4 with ammonium hydroxide. Preferably the compound of formula 4 is heated with concentrated ammonium hydroxide to a temperature of from 150° to 200° C. preferably at 180° C. in a pressure reactor.

The present invention is also the use of the compound of formula 5 for the preparation of a compound of the formula I wherein n is one which comprises (1) treating the compound of formula 5 (including the compound 5 either in its protected or unprotected form, for example,

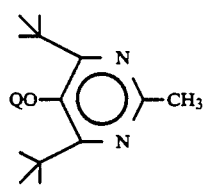

wherein Q is H or a protecting group as generally set out below) with a strong base such as butyllithium, sodium amide, LDA (lithium salt of diisopropyl amine) and the like; (2) treating the product of (1) with a compound of the formula WCHO wherein W is as defined above; and (3) dehydrating the product of (2).

The present invention is also the combined method of using the compound of formula 4 and method of using the compound of formula 5 set out immediately hereinbefore.

Under certain circumstances, understood by an ordinarily skilled artisan and as discussed below, it is necessary to protect the phenolic OH of the pyrimidine in various intermediates to give Q substituted pyrimidine which is

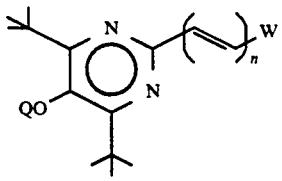

where Q is a suitable oxygen protecting group, preferably methoxyethoxymethyl (MEM) and where n=0 or 1.

The MEM group is removed later using 1) Lewis acids such as $ZnBr_2$ in halogenated solvents such as methylene chloride, chloroform, and dichloroethane at 0° to 60° C., 2) mineral acids such as HCl, HBr, or $HNO_3$ in solvents such as water, alkanols, tetrahydrofuran, dialkylethers, dioxane, glyme, diglyme at 0° to 60° C. or 3) organic acids such as acetic acid in the solvents described in 1) and 2) at 0° to 60° C.

Introduction and removal of such suitable oxygen protecting groups are well-known in the art of organic chemistry; see for example "Protective Groups in Organic Chemistry," J. F. W. McOmie, ed., (New York, 1973), pages 43ff, 95ff, J. F. W. McOmie, *Advances in Organic Chemistry*, Vol. 3, 159-190 (1963); J. F. W. McOmie, *Chem. & Ind.*, 603 (1979), and T. W. Greene, "Protective Groups in organic Synthesis", Wiley (New York) 1981, Chapters 2, 3, and 7.

Examples of suitable oxygen protecting groups are benzyl, trialkylsilyl, ethoxyethyl, methoxyethoxymethyl, methoxymethyl, trialkylsilylethyl, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although such groups may not be expressly illustrated.

The present invention is also a method of using the compound of formula 10 for the preparation of the formula I wherein n is zero which comprises treating the compound of formula 10 with ammonium hydroxide or with another agent providing ammonia in situ but preferably with ammonium hydroxide, preferably also in a manner as described above in the treatment of the compound of formula 4 for the preparation of a compound of the formula 5.

The present invention is also a process for the preparation of a compound of the formula I as defined above which comprises (A) (1) treating a compound of the formula 5 as defined above with a strong base such as butyllithium, sodium amide, LDA, and the like; (2) treating the product of (1) with a compound of the formula WCHO wherein W is as defined above, and (3) dehydrating the product of (2) to obtain a compound of the formula I wherein n is one; or alternatively (B) treating a compound of the formula 10 as defined above with ammonium hydroxide to obtain a compound of the formula I wherein n is zero.

The steps (A) and (B) are independently also the present invention. Further the steps (A)(1), (2), and (3) are independently the present invention.

The present invention is also a pharmaceutical composition for the treatment of conditions advantageously affected by the inhibition of 5-lipoxygenase alone or together with the inhibition of cyclooxygenase, preferably the inhibition of both 5-lipoxygenase and cyclooxygenase which comprises an amount effective for the treatment of the condition of a compound of the formula I and the pharmaceutically acceptable acid addition or base salt thereof together with a pharmaceutically acceptable carrier. The condition is meant to include, for example, rheumatoid arthritis, osteoarthritis, other inflammatory conditions, pain, fever, psoriasis, allergic diseases, asthma, inflammatory bowel disease, GI ulcers, cardiovascular conditions including ischemic heart disease and atherosclerosis, and ischemia-induced cell damage particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. However, overall the but preferable use is to treat inflammatory conditions.

The present invention is also a method for treatment of the condition as noted above in a mammal, including humans, suffering therefrom with a compound of the formula I or the pharmaceutically acceptable acid addition or base salt thereof, in unit dosage form. The invention also provides for use of any such compound of formula I or salt thereof in the manufacture of a medical therapeutic agent.

Pharmaceutical composition or use of the compound or salt of formula I is meant to include treatment understood to be prophylactic pertinent to the foregoing named condition.

DETAILED DESCRIPTION OF THE INVENTION

"Heteroaromatic ring" means pyridinyl, pyrimidinyl, thienyl, furyl, pyrrolyl, pyrazinyl, triazinyl, oxazolyl, isoxazolyl, pyrazolyl, pyridazinyl, imidazolyl, thiazolyl, isothiazolyl, thiadiazolyl, oxadiazolyl, triazolyl, and the like. These ring systems are meant to include rings having a lower alkyl substituent on one or more of the ring carbons, and also includes all possible regioisomers. Such regioisomers are limited by a required attachment to the pyrimidinyl group through a carbon of the ring.

"Substituted phenyl" means phenyl having one, two or three of lower alkyl, lower alkoxy, halogen, trifluoromethyl, $NR_{10}R_{11}$ wherein $R_{10}$ and $R_{11}$ are independently hydrogen or lower alkyl, $NO_2$, mercapto, hydroxy, or lower thioalkoxy.

"Substituted naphthyl" means naphthyl having one of lower alkyl, lower alkoxy, halogen, trifluoromethyl, $NR_{10}R_{11}$ wherein $R_{10}$ and $R_{11}$ are independently hydrogen or lower alkyl, $NO_2$, mercapto, hydroxy, or lower thioalkoxy.

In the compounds of formula I the term "lower alkyl", "lower alkoxy" or "lower thioalkoxy" includes an alkyl group of from one to six carbons such as methyl, ethyl, propyl, butyl, and the like and isomers thereof. Halogen is chloro, bromo or fluoro.

The compounds I of the invention may exist as tautomers which are readily determined from art recognized tautomerism.

Appropriate compounds of formula I are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as methanesulfonic acid, ethanesulfonic acid, benzenesulfonic acid, p-toluenesulfonic acid, and the like, giving the hydrochloride, sulfamate, methanesulfonate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; choline N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1–19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

The compounds of the present invention are also meant to include hydrated or solvated forms, if possible.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula I or pharmacologically acceptable salt thereof to achieve a therapeutic effect will, of course, vary both with the particular compound, the route of administration, the mammal under treatment, and the particular disorder or disease concerned. A suitable dose of a compound of formula I or pharmacologically acceptable salt thereof for a mammal suffering from, or likely to suffer from any condition as described hereinbefore is 0.1 μg–500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng-100 μg of the compound per kilogram, typically about 0.1 μg/kg.

In the case of oral dosing for the treatment or prophylaxis of arthritis or inflammation in general, due to any course, a suitable dose of a compound of formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from I to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$ 1.15 g; $KH_2PO_4$ 0.2 g; and KCl, 0.2 g/l ). Cells are finally suspended in PBS containing 1.0 Mm calcium at a density of $2 \times 10^6$ cells/ml. Cells are incubated with and without test agent (in DMSO) (1% DMSO is without effect on arachidonic acid metabolism) for ten minutes at room temperature. Calcium ionophore A23187 (5 μM) is added and cells are incubated for seven minutes at 37° C. The reaction is stopped by chilling the tubes on ice for ten minutes. Cells are separated by centrifugation and the supernatant is stored at −20°. Aliquots (100 μl) are analyzed for $LTB_4$ and $PGF_{2\alpha}$ using radioimmunoassay kits as provided by the supplier.

Table 1 contains biochemical data obtained from this whole cell assay expressed as % inhibition at a 10 μM dose but which may also provide a result that may be expressed as $IC_{50}s$ which are calculated as the amount of test compound causing 50% inhibition of $LTB_4$ or $PGF_{2\alpha}$ formation.

TABLE 1

| Example | ARBL | ARBC $IC_{50}$ (μM) |
| --- | --- | --- |
| 1 | 100% @ 10 μM | 85% @ 10 μM |
| 3 | N* | 60% @ 10 μM |

*<40% inhibition at 10 μM

Carrageenan-Induced Rat Foot Paw Edema-2 (CFE-2) Assay: Protocol

Carrageenan solution (1% w/v) is prepared by dissolving 100 mg carrageenan (Marine Colloidal Div., Springfield, N.J.) in 10 mL of sterile saline (0.9%) solution (Travenol). The solution is vortexed for 30 to 45 minutes. Animals are dosed with compound one hour before carrageenan challenge. Foot paw edema is induced by injecting 0.10 ml of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured five hours after carrageenan. The difference between the five-hour and the initial paw volume is expressed as delta edema. The delta edema for each test group of animals is used to calculate the percent inhibition of edema achieved by the compound at the test dose compared with the vehicle control group. The $ID_{40}$ (the dose at which swelling is inhibited by 40%) is calculated by probit analysis for the dose at which 40 percent inhibition occurs.

TABLE 2

| Example | Salt Form | % Inhibition of Edema |
|---------|-----------|----------------------|
| 1 | Methanesulfonate | 45% at 30 mg/kg |

Mycobacterium—Induced Rat Footpad Edema Assay (MFE): Protocol

Mycobacterium butyricum (5 mg/mL) is suspended in paraffin oil by sonication for ten minutes in an ice bath. Footpad edema is induced on Day 0 by injecting 0.1 ml of the Mycobacterium mixture into the left hindpaw of lightly anesthetized rats. Swelling in the injected hindpaw is determined by mercury plethysmography 72 hours after injection. Groups of rats are treated with test compounds (suspended in 0.5% hydroxypropyl methylcellulose with 0.2% Tween-80) or vehicle one hour before Mycobacterium injection and on Days 1 and 2. Inhibition of swelling is determined by comparing the change in hindpaw volume in compound- and vehicle-treated rats. An $ID_{40}$ (the dose at which swelling is inhibited by 40%) is calculated by probit analysis.

Gastric Ulcerogenicity (UD): Protocol

Male outbred Wistar rats (100-250 g) are fasted for 24 hours. After fasting, test compounds are administered orally (in 2 ml/kg of 0.5% hydroxypropyl methylcellulose) and the rats are denied access to food and water for six more hours. The rats are then sacrificed with $CO_2$ so that the stomachs can be removed, opened along the greater curvature, and evaluated for the presence of gastric ulcers. Results are expressed as the percent of rats with gastric ulcers at a given dose or as the $UD_{50}$ (the dose which causes ulcers in 50% of the rats).

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprofen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —$CH(CH_3)$ COOH or —$CH_2CH_2COOH$ group (which optionally can be in the form of a pharmaceutically acceptable salt group, e.g., —$CH(CH_3)COO^-NA^+$ or —$CH_2CH_2COO^-Na^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free—$CH_2COOH$ group (which optionally can be in the form of a pharmaceutically acceptable salt group, e.g. —$CH_2COO^{31} Na^+$), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

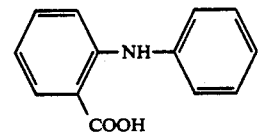

which can bear a variety of substituents and in which the free —COOH group can be in the form of a pharmaceutically acceptable salt group, e.g., —$COO^{-Na+}$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

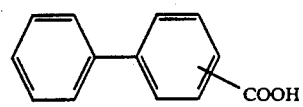

which can bear a variety of substituents and in which the free —COOH group can be in the form of a pharmaceutically acceptable salt group, e.g., —COO+Na+.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

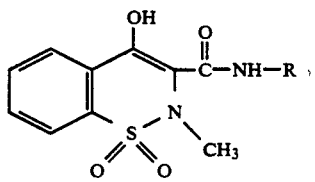

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, difisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepacr isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compounds of the formula I and their salts are prepared generally by the following processes and constitute a further aspect of the present invention.

The compounds are prepared by the following schemes.

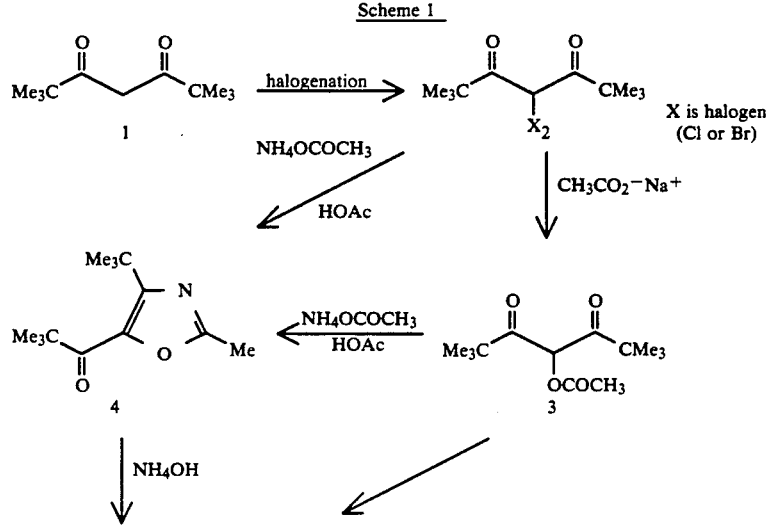

Scheme 1

Scheme 1

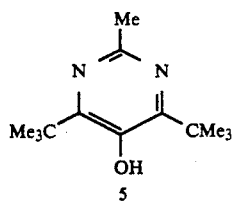

Scheme 2

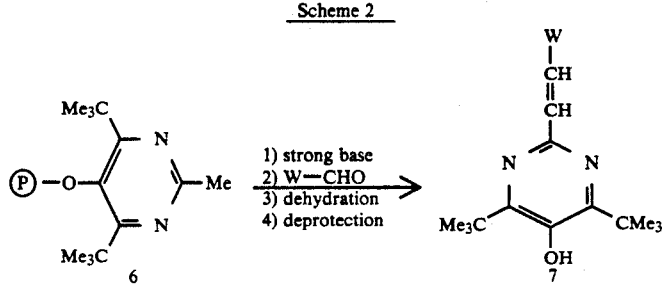

Scheme 3

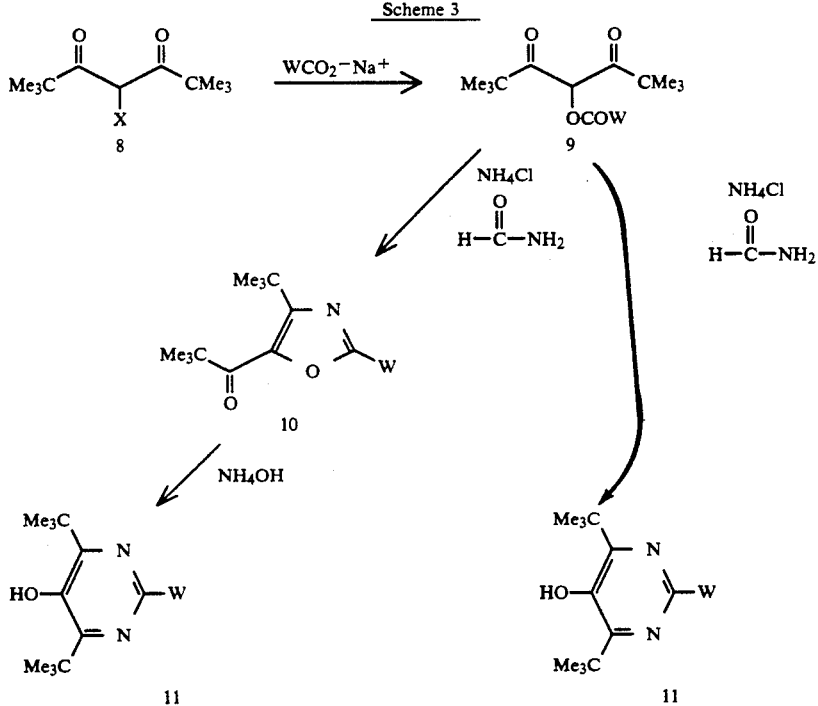

Generally, the Schemes 1, 2 and 3 are carried out as follows:

Description of Scheme 1

Compound of the formula 3 is prepared from the known haloketone 2 (C. W. Shoppee and D. Stevenson, *J. Chem. Soc. Perkin I*, p. 3015, 1972) by reaction with a salt of acetic acid such as sodium or potassium acetate in a solvent such as DMSO at a reaction temperature of 18° C. to 60° C., or in a solvent such as acetic acid at reflux. Acetoxydiketone 3 is converted to oxazole 4 by treatment with an ammonium salt such as ammonium chloride or preferably ammonium acetate in a solvent such as acetic acid at reflux for 1 to 16 hours or in a solvent such as formamide at 100° to 200° C. for 1 to 6 hours. Alternatively, 2 is converted directly to 4 by treatment with acetamide or ammonium acetate in a solvent such as acetic acid at reflux. The oxazole 4 is converted to pyrimidine 5 by treatment with ammonia or an ammonium salt at elevated temperature. Preferably 4 is reacted with concentrated ammonium hydroxide at 150° to 190° C. in a pressure reaction vessel for 6 to 72 hours. 5 is also prepared by reaction of 3 with an ammonium salt such as NH$_4$Cl or NH$_4$OAc in a solvent such as formamide at a temperature of 180° to 200° C. for longer periods of time such as overnight to 1 week.

Description of Scheme 2

The protected pyrimidine 6 is deprotonated using a strong base such as sodium amide or butyllithium in a suitable solvent such as THF, ether, or hexane at −78° C. to room temperature. The anion generated above is reacted with an aldehyde, followed by dehydration, using sodium acetate in acetic anhydride at 100° to 190° C. Deprotection is done by methods known in the literature for the particular protecting group.

Description of Scheme 3

The halodiketone 8 is reacted with a salt of the carboxylic acid WCOOH, where W is as defined above, preferably the sodium or potassium salt in a solvent such as DMSO or THF or MEOH or mixtures thereof at a temperature of room temperature to 60° C. to give intermediate 9. 9 is reacted with an ammonium salt preferably ammonium chloride or the ammonium salt of WCOOH in a solvent such as formamide at 100° to 190° C. or using WCOOH as a solvent. The oxazole 10 is converted to pyrimidine 11 by treatment with ammonia or an ammonium salt at elevated temperature, preferably using concentrated ammonium hydroxide at 150° to 190° C. in a pressure reaction vessel. In some cases treatment of 9 with an ammonium salt such as ammonium chloride or the ammonium salt of WCOOH in a solvent such as formamide at elevated temperatures such as 100° to 190° C. gives pyrimidine 11.

One of skill in the art would recognize variations in the sequence and would recognize variations in the appropriate reaction conditions from the analogous reactions shown or otherwise known which may be appropriately used in the processes above to make the compounds of the Formula I herein. Further, starting materials are known or can be prepared by known methods.

The products of the reactions described herein are isolated by conventional means such as extraction, distillation, chromatography, and the like.

The invention is further elaborated by the representative examples as follows. Such examples are not meant to be limiting.

EXAMPLE 1

[E]-4,6-Bis(1,1-dimethylethyl)-2-[[2-(3-pyridinyl)]-ethenyl]-5-pyrimidinol

A mixture of 4,6-bis(1,1-dimethylethyl)-5-[(2-methoxyethoxy)methoxy]-α-(3-pyridinyl)-2-pyrimidineethanol (350 mg), sodium acetate (10 g) and acetic anhydride (7 ml) in toluene (100 ml) is heated at reflux for 8 hours. The reaction mixture is cooled and the solvent is evaporated. Dichlorobenzene (30 ml) is added and the reaction mixture is heated at 190° C. for 30 minutes. The reaction mixture is cooled and partitioned between ethyl acetate and water. The aqueous layer is adjusted to pH 4 with 1 N HCl. The organic layer is collected and evaporated. Purification of the residue by flash chromatography (silica, 1:1 ethyl acetate/hexane) followed by recrystallization from hexane gives pure 4,6-bis(1,1-dimethylethyl)-2-[[2-(3-pyridinyl)]ethenyl]-5-pyrimidinol (130 mg, 40%); mp 150°–151° C.

The following compounds are prepared according to the procedure of Example C and Example 1.

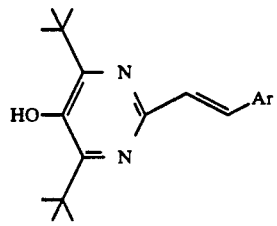

| Example | Ar | Prepared From | MP | % Yield |
|---|---|---|---|---|
| 2 | —C₆H₅ (phenyl) | Benzaldehyde | Oil [salt.HCl.½ H₂O mp 199–200° C. (dec.)] | 48% |
| 3 | 3-methylisothiazol-5-yl | 3-methylisothiazole-5-carboxaldehyde | 161–162° C. | 12% |

EXAMPLE 4

4,6-[bis(1,1-dimethylethyl)]-5-hydroxy-2-(3-pyridinyl)-pyrimidine

A solution of 1-[4-(1,1-dimethylethyl)-2-(3-pyridinyl)-5-oxazolyl (2, 2-dimethyl) -1 -propanone (510 mg, 1.8 mmol) in methanol (2 mL) is transferred to a glass-lined steel bomb. Ammonium hydroxide (25 mL) is added and the reaction mixture is heated at 180° C. for 16 hours. The reaction mixture is cooled and the product is collected by filtration. Recrystallization from ethyl acetate gives pure 4,6-[bis(1,1-dimethylethyl))-5-hydroxy-2-(3-pyridinyl)pyrimidine (180 mg, 35%) mp 178°–180° C.

EXAMPLE 5

1)-2-methyl-5-oxazolyl]-2,2-dimethyl-1-propanone

A solution of 4-(acetyloxy)-2,2,6,6-tetramethyl 3,5-heptanedione (22 g, 0.09 mol) in acetic acid (100 mL) is treated with ammonium acetate (44 g). The reaction mixture is heated at reflux overnight. The reaction mixture is diluted with water and neutralized (to pH 5) by the addition of aqueous sodium hydroxide. The product is extracted into ethyl acetate (3×150 mL) and the combined organic layers are washed with 0.1 N NaOH, water, and then brine. The organic layer is dried and evaporated. The residue is taken up in hexane (50 mL) and applied to a pad of silica gel (500 g). The silica pad is eluted with hexane (100 mL). Then the product is eluted from the silica with hexane/ethyl acetate (4:1) to give 18.6 g (91%) of 1-[4-(1,1-dimethylethyl)-2-methyl-5-oxazolyl]-2,2-dimethyl-1-propanone as an oil.

$^1$H-NMR (CDCl$_3$)δ 2.60 (s, 3H, 2-Me), 1.35 (s, 9H, tbu), 1.31 (s, 9H, tbu)

$^{13}$C-NMR (CDCl$_3$)δ 195.8, 159.3, 157.6, 143.6, 44.2, 32.7, 28.4, 26.6

EXAMPLE 6

4,6-Bis(1,1-dimethylethyl)-5hydroxy-2methyl pyrimidine

A mixture of 1-[4-(1,1-dimethylethyl)-2-methyl-5-oxazolyl]-2,2-dimethyl-1-propanone (8.5 g, and concentrated ammonium hydroxide (100 ml) is heated at 180° C. for 36 hours in a steel bomb. The reaction mixture is cooled and the excess ammonia is evaporated on the rotovap. The pH of the resulting mixture is adjusted to pH 6 with concentrated HCl with ice bath cooling. The product is extracted into ether (3×250 mL) and the organic layer is dried (MgSO$_4$) and evaporated. The residue is purified by flash chromatography (silica, 7% EtOAc/hexane) to give pure 4,6-bis(1,1-dimethylethyl)-5-hydroxy-2-methylpyrimidine (6.35g, 75%) as a partial hydrate; mp 62°-65° C.

$^1$H-NMR (d$_6$-DMSO) δ 7.76 (br, 1H, OH), 2.45 (s, 3H, CH$_3$), 1.36 (s, 18H, t-bu).

$^{13}$C-NMR (CDCl$_3$)δ 161.2, 157.5, 145.1, 37.0, 28.7, 25.4.

The compound is further characterized by conversion to its acetyl derivative, mp 45°-47° C.

EXAMPLE 7

4,6-Bis-(1,1-dimethylethyl)-5-[(2-methoxyethoxy)-methoxy]-2-methylpyrimidine 4,6-Bis(1,1-dimethylethyl)-5-hydroxy-2-methyl pyrimidine (9.8 g, 44.1 remoles) is dissolved in 100 mL of tetrahydrofuran and added dropwise to a suspension of sodium hydride (1.2 g, 48.5 remoles) in THF (50 mL) at 0° C. The reaction mixture is warmed to room temperature over 15 minutes. 2-Methoxyethoxymethyl chloride (7.1 g, 57.3 mmoles) is added to the reaction mixture at room temperature. After being stirred at room temperature for 4 hours, the reaction is quenched by the addition of saturated ammonium chloride and the tetrahydrofuran is evaporated. The organics are extracted into 300 mL of ether. The ether is washed with 100 mL of brine and dried over magnesium sulfate. Evaporation of the solvent gives the crude product which is purified by flash chromatography (silica, 10% ether/hexane). Yield of 4,6-bis(1,1-dimethylethyl)-5-[(2-methoxyethoxy)methoxy]-2-methylpyrimidine=11.3 g (82%) as a clear oil.

$^1$H-NMR-(CDCl$_3$)δ 4.96 (s, 2H, 0—CH$_2$—0), 3.93 (m, 2H), 3.60 (m, 2H), 3.39 (s, 3H, 0—CH$_3$), 2.54 (s, 3H, CH$_3$), 1.40 (s, 18H, C(CH$_3$)$_3$). C$^{13}$-NMR(CDCl$_3$)δ 169.2, 159.8, 145.7, 99.9, 71.5, 69.4, 58.9, 38.2, 30.0, 25.2.

EXAMPLE 8

4,6-Bis(1,1-dimethylethyl)-5-[(2-methoxyethoxy)-methoxy]-α-(3-pyridinyl)-2-pyrimidineethanol n-Butyllithium (1.5 mL of 1.6M solution in hexane, 2.4 mmol) is added dropwise to a solution of 4,6-bis(1,1-dimethylethyl)-5-[(2-methoxyethoxy)-methoxyl-2-methylpyrimidine (750 mg, 2.4 mmol) in dry THF (12 mL) at 0° C. under an atmosphere of dry nitrogen. The reaction mixture is stirred at room temperature for 30 minutes and then cooled to −78° C. A solution of pyridine 3-carboxaldehyde (250 mg, 2.4 mmol) in dry THF (1 mL) is added dropwise. The reaction mixture is stirred at room temperature for 3 hours and then is quenched by the addition of saturated aqueous ammonium chloride. The product is extracted into ether. The organic layer is dried (MgSO$_4$) and evaporated to give crude 4,6-bis(1,1-dimethylethyl)-5-[(2-methoxyethoxy)-methoxy]-α-(3-pyridinyl)- 2-pyrimidineethanol (500 mg, 50%) which is not further purified, but used directly in the next reaction.

EXAMPLE 9

1-(2,2-Dimethyl-1-oxopropyl)-3,3-dimethyl-2-oxobutyl-3-pyridinecarboxylate

A mixture of 4-bromo-2,2,6,6-tetramethyl-3,5-heptanedione (2.6 g, 10 mmol) and 3 g of the sodium salt of nicotinic acid in DMSO (4 ml) is stirred at room temperature for 30 minutes. The reaction mixture is partitioned between water and ether. The organic layer is washed with water (5×100 mL) and is dried (MgSO$_4$) and evaporated.

Recrystallization from hexane gives pure 1-(2,2-dimethyl-1-oxopropyl)-3,3-dimethyl-2-oxobutyl-3-pyridinecarboxylate (1.9 g, 62%); mp 90°-91° C.

EXAMPLE 10

1 [4-(1,1-dimethylethyl)-2-(3-pyridinyl)-5-oxazolyl]-2,2-dimethyl-1-propanone

A solution of 1-(2,2-dimethyl-1-oxopropyl)-3,3-dimethyl-2-oxobutyl-3-pyridinecarboxylate (1.5 g, 4.9 mmol) in formamide (20 mL) is treated with ammonium chloride (3 g) and the reaction mixture is stirred at 150° C. overnight. The reaction mixture is cooled, diluted with water and extracted with ether. The organic layer is washed with water (3×50 mL), dried over MgSO$_4$ and evaporated to give the desired oxazole (1.1 g, 78%) containing about 10% of 4,6-[bis(1,1-dimethylethyl)]-5-hydroxy-2-(3-pyridinyl)pyrimidine. The contaminating pyrimidine crystallizes upon the addition of hexane to give the desired oxazole in the mother liquor. The oxazole is isolated as an oil and is converted to the pyrimidine without further purification.

What is claimed is:
1. A compound of the formula I

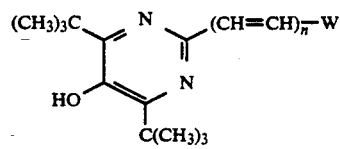

or a pharmaceutically acceptable salt, or hydrate thereof; wherein n is an integer of zero or one;
W is phenyl, phenyl having one, two or three of lower alkyl, lower alkoxy, halogen, trifluoromethyl, NR$_{10}$R$_{11}$ wherein R$_{10}$ and R$_{11}$ are independently hydrogen or lower alkyl, NO$_2$; mercapto, hydroxy, or lower thioalkoxy, naphthyl, or naphthyl.

2. A compound of claim 1 wherein n is zero.
3. A compound of claim 1 wherein n is one.

4. A compound of claim 3 which is 4,6-bis(1,1-dimethylethyl)-2-[(2-phenyl)ethenyl]-5-pyrimidinol.

5. A pharmaceutical composition for the treatment of a condition advantageously affected by the inhibition of 5-lipoxygenase, cyclooxygenase or both 5-lipoxygenase and cyclooxygenase which comprises an amount effective for the treatment of the condition of the compound of claim 1 and a pharmaceutically acceptable carrier.

6. A method of treating inflammation in a human in need of such treatment which comprises administering a compound of claim 1 in unit dosage form.

7. A method of treating allergy in a human in need of such treatment which comprises administering a compound of claim 1 in unit dosage form.

8. A method of treating ulcers in a human in need of such treatment which comprises administering a compound of claim 1 in unit dosage form.

9. A pharmaceutical composition which comprises a compound of claim 1 and a nonsteroidal antiinflammatory drug in an amount wherein a ratio of the weight range is from 1000:1 to 1:1000.

* * * * *

UNITED STATES PATENT AND TRADEMARK OFFICE
CERTIFICATE OF CORRECTION

PATENT NO. : 5,302,597
DATED : April 12, 1994
INVENTOR(S) : Connor et al

It is certified that error appears in the above-indentified patent and that said Letters Patent is hereby corrected as shown below:

On the title page: Item [21] Appl. No. : 875,151" should be
-- 08/075,151 --.

Signed and Sealed this

Twenty-sixth Day of July, 1994

Attest:

BRUCE LEHMAN

*Attesting Officer*  *Commissioner of Patents and Trademarks*